United States Patent [19]

Di Guiseppi et al.

[11] Patent Number: 5,164,796

[45] Date of Patent: * Nov. 17, 1992

[54] APPARATUS AND METHOD FOR DETECTION OF MICROORGANISMS

[75] Inventors: James L. Di Guiseppi; Thurman C. Thorpe, both of Durham, N.C.

[73] Assignee: Akzo N.V., Arnhem, Netherlands

[*] Notice: The portion of the term of this patent subsequent to Jul. 31, 2007 has been disclaimed.

[21] Appl. No.: 649,147

[22] Filed: Dec. 1, 1991

Related U.S. Application Data

[63] Continuation-in-part of Ser. No. 168,291, Mar. 15, 1988, Pat. No. 4,945,060, and a continuation of Ser. No. 351,476, May 15, 1989, abandoned.

[51] Int. Cl.$^5$ .................. G01N 21/55; G12M 1/00; G12M 1/34
[52] U.S. Cl. .................. 356/445; 435/287; 435/291; 435/34; 422/52
[58] Field of Search .............. 356/345, 346, 412, 445, 356/416, 39; 250/341; 435/84, 291; 422/68

[56] References Cited

U.S. PATENT DOCUMENTS

| | | | |
|---|---|---|---|
| Re. 31,879 | 5/1985 | Lübbers | 422/68 |
| 2,880,070 | 3/1959 | Gilbert et al. | 436/55 |
| 3,067,015 | 12/1962 | Lawdermilt | 422/56 |
| 3,676,679 | 7/1972 | Waters | 250/380 |
| 3,853,712 | 12/1974 | House et al. | 435/285 |
| 3,998,591 | 12/1976 | Eckfeldt | 356/445 |
| 4,004,981 | 1/1977 | Hurni et al. | 435/285 |
| 4,073,691 | 2/1978 | Ahnell et al. | 435/34 |
| 4,101,383 | 7/1978 | Wyatt et al. | 435/5 |
| 4,152,213 | 5/1979 | Ahnell | 435/34 |
| 4,182,656 | 1/1980 | Ahnell et al. | 435/34 |
| 4,236,211 | 11/1980 | Arvesen | 364/413 |
| 4,289,248 | 9/1981 | Lynn | 215/330 |
| 4,306,877 | 12/1981 | Lübbers | 422/68 |
| 4,407,959 | 10/1983 | Tsuji et al. | 435/291 |
| 4,456,380 | 6/1984 | Kondo et al. | 356/418 |
| 4,568,518 | 2/1986 | Wolfbeis | 422/56 |
| 4,672,039 | 6/1987 | Lundblom | 435/291 |
| 4,698,308 | 10/1987 | Ikeda | 435/291 |
| 4,780,191 | 10/1988 | Romette et al. | 204/403 |
| 4,784,947 | 11/1988 | Noeller | 435/33 |
| 4,889,992 | 12/1989 | Hoberman | 250/343 |
| 4,945,060 | 7/1990 | Turner et al. | 435/291 |
| 4,971,900 | 11/1990 | Ahnell | 435/34 |
| 5,047,331 | 9/1991 | Swaine et al. | 435/29 |
| 5,094,955 | 3/1992 | Calandra et al. | 435/291 |

FOREIGN PATENT DOCUMENTS

| | | |
|---|---|---|
| 472420 | 5/1976 | Australia . |
| 0104463 | 4/1984 | European Pat. Off. . |
| 0118274 | 9/1984 | European Pat. Off. . |
| 0255087 | 2/1988 | European Pat. Off. . |
| 301699 | 2/1989 | European Pat. Off. . |
| 333253 | 9/1989 | European Pat. Off. . |
| 2603684 | 9/1987 | France . |
| 57-207861 | 12/1982 | Japan . |
| 61-149818 | 7/1986 | Japan . |
| 8100304 | 2/1981 | World Int. Prop. O. . |

OTHER PUBLICATIONS

McFaddin, *Biochemical Tests for Identification of Medical Bacteria,* pp. 187–193 and 108–117 (1976).
"Optical Sensors for pH and Blood Gas Analysis," Marsoner et al., IFCC Workshop, Helsinki, 1985.
"Simplex Optimization of a Fiber-Optic Ammonia Sensor Based on Multiple Indicators," Rhines et al., 60 Anal. Chem. 76–81 (1988).
"Fiber-Optic Fluorescing Sensor for Ammonia," Wolfbeiss et al., 185 Analytica Chemia ACTA, 321–327 (1986).

*Primary Examiner*—Vincent P. McGraw
*Assistant Examiner*—LaCharles P. Keesee
*Attorney, Agent, or Firm*—William M. Blackstone; Donna Bobrowicz

[57] ABSTRACT

An instrument for monitoring the color change of an indicator element sealed within a sterile vessel and exhibiting a color change in response to a change in the pH of $CO_2$ level within the sterile vessel as a result of microbacterial growth within a specimen contained in the sterile vessel. The present invention includes means for continuously monitoring the absolute value of the pH and or $CO_2$ level within the vessel and or monitoring the rate of change of the absolute value of the pH level.

28 Claims, 7 Drawing Sheets

APPARATUS AND METHOD FOR DETECTION OF MICROORGANISMS

CROSS-REFERENCE TO RELATED APPLICATION

This application is a continuation-in-part of U.S. application Ser. No. 07/168,291 filed Mar. 15th, 1988, now U.S. Pat. No. 4,945,060, and also a continuation of U.S. application Ser. No. 07/351,476 filed May 15th, 1989, and now abandoned.

BACKGROUND OF THE INVENTION

The present invention relates to methods and devices for detection of bacterial growth within a specimen. More particularly, the present invention relates to an electronic apparatus for detecting microorganism growth within a sample through monitoring of an indicating element exposed to the sample growth.

The presence of microbial contamination in a clinical specimen is conventionally determined by culturing the specimen in the presence of nutrients and detecting microbial activity through changes in the specimen or in the atmosphere over the specimen after a period of time. For example, in U.S. Pat. No. 4,182,656, to Ahnel, et al., the sample is placed in a container with a culture medium comprising a Carbon 13 fermentable substrate. After sealing the container and subjecting the specimen to conditions conducive to biological activity, the ratio of Carbon 13 to known Carbon 12 in the gaseous atmosphere over the specimen is determined and compared with the initial ratio. In U.S. Pat. No. 4,152,213, a method is claimed by which the presence of oxygen consuming bacteria in a specimen is determined in a sealed container by detecting a reduction in the amount of oxygen in the atmosphere over the specimen through monitoring the gas in the container. U.S. Pat. No. 4,073,691 provides a method for determining the presence of biologically active agents, including bacteria, in a sealed container, containing a culture medium by measuring changes in the character of the gaseous atmosphere over the specimen after a period of time.

A method for non-invasive detection of $CO_2$ changes in the gaseous atmosphere is taught by Suppman, et al. as disclosed in EPO Application 83108468.6, published Apr. 4th, 1984. The methods and apparatus described in these and other publications all require either a radiometric method or the invasion of the sealed container to measure changes in the gaseous atmosphere after culturing or require that the container be manufactured of special materials that permit unimpeded passage of infrared light.

Other known methods for measuring microbial contamination of a specimen, particularly blood cultures, include measuring minute changes in temperature, pH, turbidity, color, bioluminescence, and impedance. Generally, these methods determine microbial contamination by detecting bacterial metabolic by-products. Microbial contamination may also be assessed by subculturing and/or staining. Of these methods, only impedance, radiometry, and infrared spectrometry provide the possibility of automated processing of a clinical specimen. Except for impedance and infrared measurements, these procedures also require entering the container in order to make a measurement on the liquid specimen or the gaseous atmosphere over the specimen.

In addition to the likelihood of contamination and creating the likelihood of altering the constituency of the atmosphere over the specimen each time the determination is made, these methods do not permit taking measurements continuously or easily over short-time intervals for an extended period of time. This is a significant disadvantage as the rate of growth of contaminating organisms differs, depending on the organism and the number of organisms in the original sample, such that it cannot be predicted when detectable changes in the atmosphere or fluid sample will be presented by a contaminated specimen.

In a related problem, when contamination is determined by pH changes in the liquid sample, various metabolic products will effect the pH of the sample differently. For example, the production of ammonia will raise the pH, while the production of $CO_2$ will lower it. Different growth rates of different contaminating organisms could result in a pH increase at one time and a decrease at another time. This variable increase-decrease would not be detected if the pH is measured at widely-spaced intervals. Another source of error when detecting changes by pH measurement in whole blood samples, particularly when an indicator is the means for pH determination, is the likelihood that the appearance of the indicator can be affected or obscured by the presence of blood cells. Colorimetric indicators can only be effectively used if errors caused by the nature of the specimen can be prevented from influencing the appearance of the dye.

SUMMARY OF THE INVENTION

It is an object of the present invention to provide an apparatus for continuous monitoring of changes in the pH or $CO_2$ levels within a specimen containing a culture for microbial growth.

It is another object of the present invention to provide an apparatus for monitoring pH or $CO_2$ changes in a specimen within a sealed container, without entering the container during the monitoring process.

It is a further object of the present invention to provide a pH and/or $CO_2$ indicator which provides continuous indication of pH or $CO_2$ levels and is unaffected by the presence of colored constituents within the growth medium.

Another object of the present invention is to provide analysis of the variance in pH and/or $CO_2$ on a continuously monitored basis.

A further object of the present invention is to monitor both the absolute pH value and the rate of change of pH. These and other objects of the present invention are accomplished by providing an apparatus for detecting the presence of microorganisms in clinical specimen, such as blood or other body fluids, by culturing the specimen with a sterile growth medium in a transparent, sealed, sterile container. The presence of microorganisms is determined by detecting or measuring changes in the pH of the specimen or the production of $CO_2$ within a specimen using a disposable sensor affixed to the interior surface of the container. According to this invention, microorganisms can be detected in the presence of interfering materials, such as large concentrations of red blood cells, through non-radiometric and non-invasive means. As the level of pH and/or $CO_2$ within the specimen changes, the light reflecting and/or absorbing characteristics of the disposable sensor will alter correspondingly. The quantity of alteration of the reflective properties of the sensor is detected by an emission and receiving mechanism which supplies signals to a device for monitoring the quantity of visible reflection/absorption and the rate of change. The rate and quantity is then analyzed to predict and determine the presence of microbial growth within the specimen or sample. The sensor can be sampled and/or monitored continuously or at frequent time intervals allowing for the collection of a detailed characteristic of the quantity and rate of sensor change.

A more complete appreciation of the invention and many of its advantages thereof will be readily perceived as the invention becomes better understood by reference to the following detailed description when considered in connection with the accompanying figures.

DESCRIPTION OF EXEMPLARY EMBODIMENTS

Figure 1:
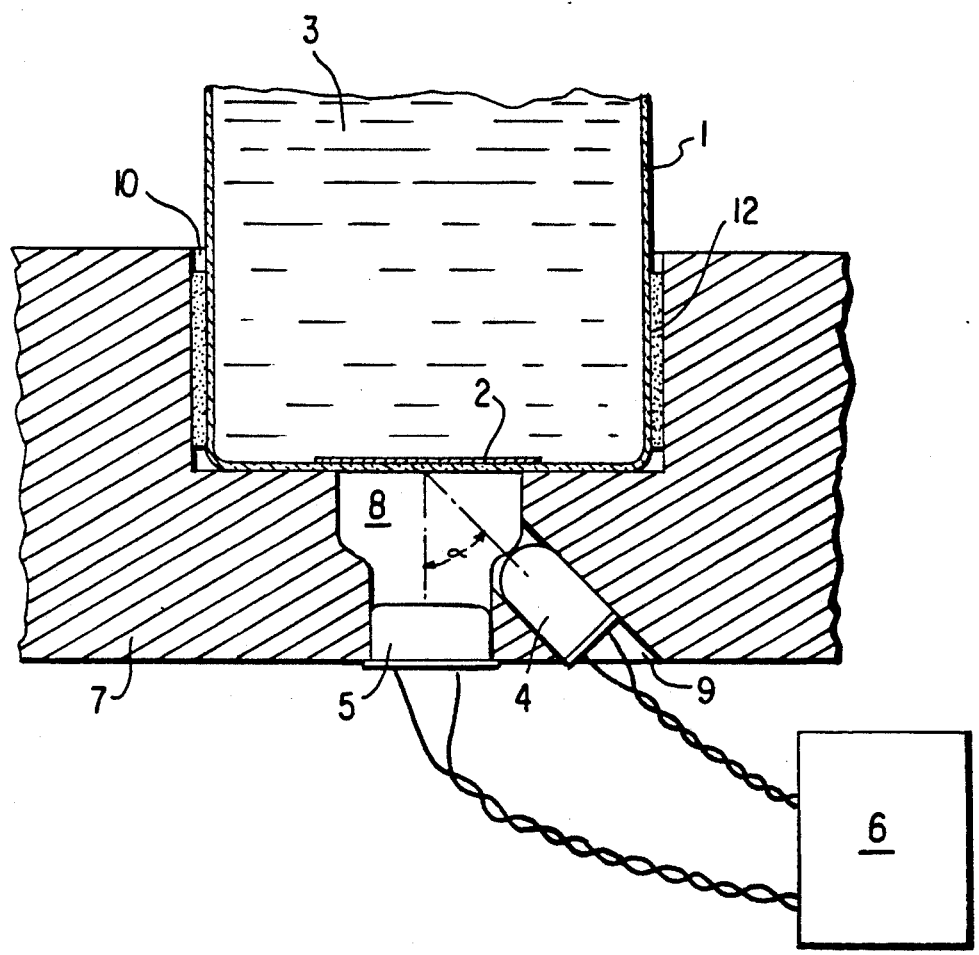
FIG. 1 is a cross-sectional view of the specimen jar and photodetector arrangement.
Figure 2:
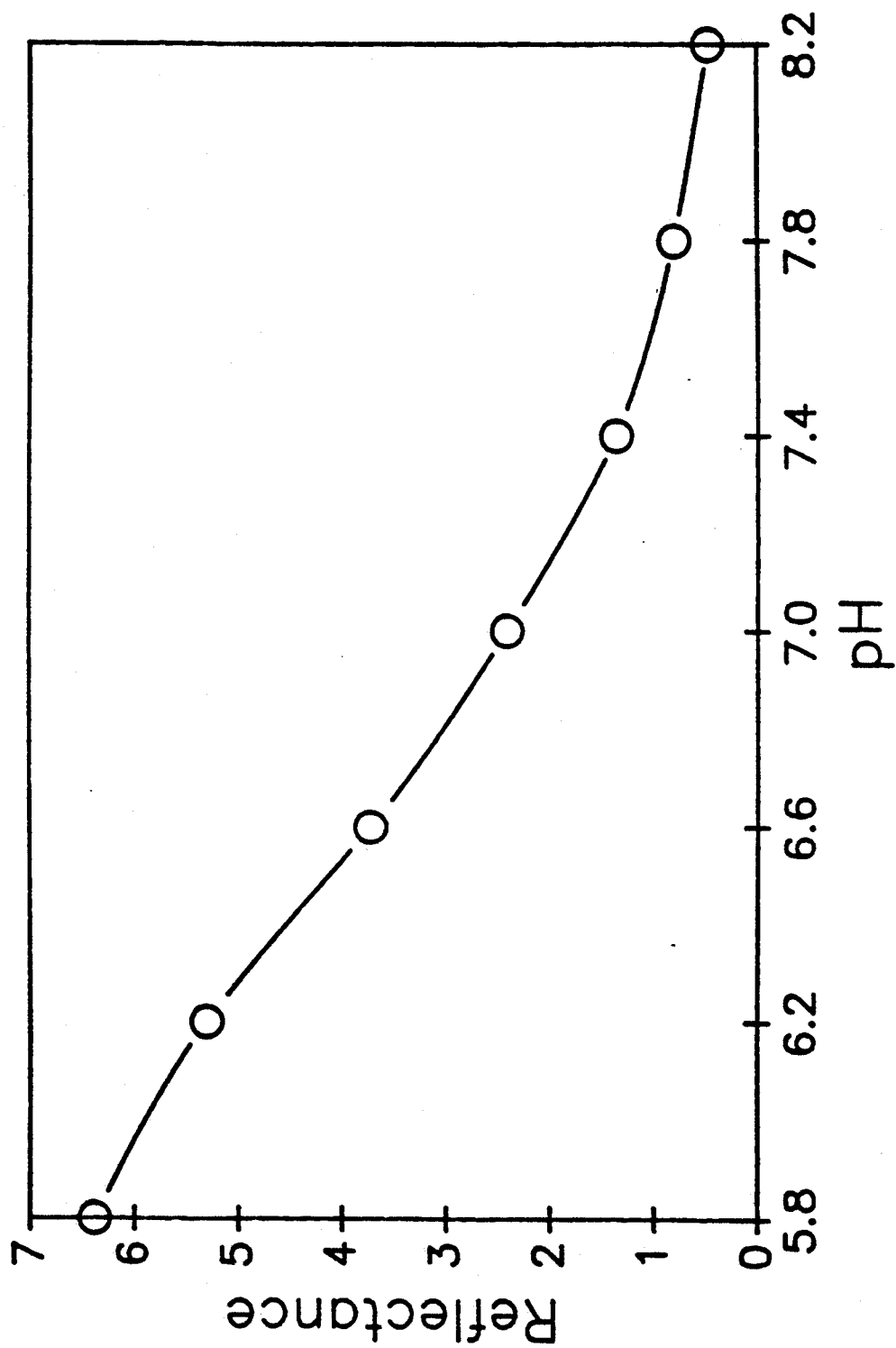
FIG. 2 is a graph showing the characteristic relation between reflectance of the sensor and the pH of the sample.
Figure 3:
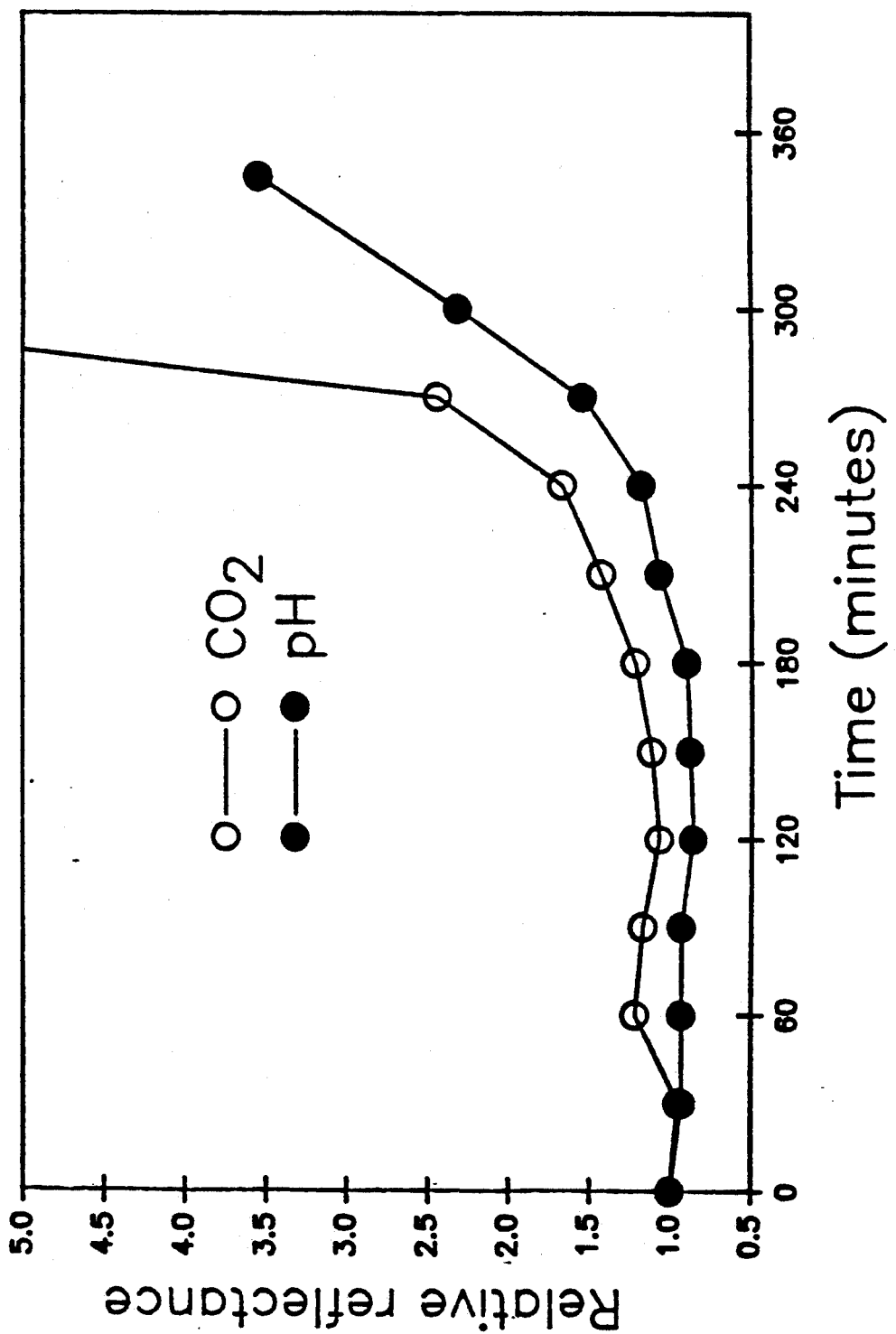
FIG. 3 is a graph illustrating a characteristic which is exemplative of the pH and $CO_2$ changes in a sample caused by the growth of *E. coli* bacteria.
Figure 4:
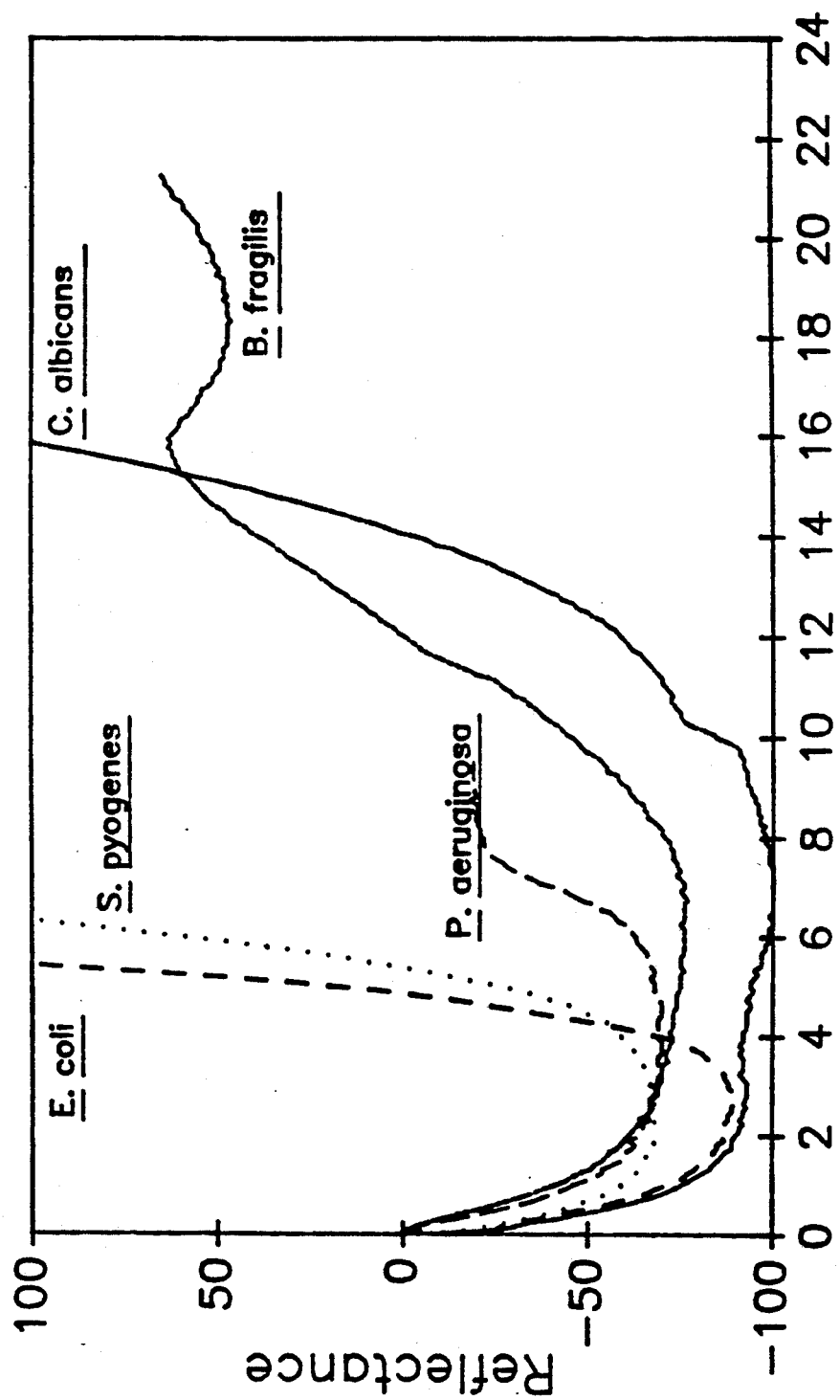
FIG. 4 is a graph illustrating the change in reflectance of a variety of microorganisms over time as measured by the present invention.

The apparatus and device of the invention provide a non-invasive means for detecting the presence of microorganisms in a clinical specimen such as blood samples or other bodily fluids, by measuring an increase in metabolic products produced by microorganisms. A specimen is added to a specially-formulated medium that enhances the production of certain microbial metabolic products. As illustrated in FIG. 1, the specimen and the formulated medium 3 are housed in a culture bottle or container 1 for incubation. The container 1 is sealed by a top, which is not illustrated.

A unique disposable sensor or indicator 2 is located within the bottle 1 positioned against one of its interior walls. The sensor 2 comprises a solid composition or membrane which is referred to as the attachment or support medium and an indicator medium mounted on or within the support medium. In this manner, the sensor 2 is placed flush against the inside surface of container 1 such that the indicator medium is visible from the outside, and is sealed against cells, proteins, or other solids or opaque or colored components of the specimen or medium from being introduced between the indicator 2 and the container 1 surface. This will prevent any objects from coming between the indicator 2 and the detector mechanism 4 and 5. In certain embodiments, the indicator 2 is separated from the specimen and its growth medium 3 by a membrane or solid layer that permits the passage of gas molecules, but prevents the passage of ions from the fluid. In this manner, the indicator 2 will be exposed to changes in pH or $CO_2$ as desired, but will not be directly exposed to the medium 3.

Specimen of body fluids such as blood, containing as few as one organism per milliliter can be detected using this invention. Such specimen require up to seven days incubation before the population of organisms reaches a critical level, or an increase in metabolic products can be measured. It has been found through operation of the present invention that a concentration of $10^6$ CFU/ml for certain types of organisms provided measurable levels in pH or $CO_2$. All organisms showed measurable results at concentrations of $10^7$ to $10^8$ CFU/ml.

The invention is unique and advantageous in several respects:

(1) the microbial metabolic products are measured in the liquid phase of the culture bottle rather than in the atmosphere over the specimen, (2) the unique disposable sensor 2 being affixed to the interior surface of the bottle 1, measurements can be made from outside of the transparent wall of the bottle 1 without having to violate the integrity of the bottle 1, (3) the external measurements can be made by visual inspection or with an instrument that measures the reflectance of the sensor 2, (4) opaque or colored components in the specimen 3 do not interfere with the ability of the sensor 2 to detect and indicate changes in the pH and or $CO_2$ levels, (5) a high concentration of indicator molecules is maintained within a small volume, i.e., on the membrane, such that a color change can be easily observed, (6) observation of the sensor 2 can be effected essentially continuously through sampling over closely-spaced time intervals since there is no invasive sampling or vessel manipulation required, and (7) a characteristic representative of the absolute level and rate of change of pH or $CO_2$ can be developed from the continuous monitoring.

The nutritional components that constitute a complex microbial medium influence the metabolic pathways used by microorganisms. Organic acids, bases and various gases are produced in proportions dependent upon the nutrients available. These products also vary from species-to-species of microorganisms. The presence of these products in the liquid medium can change its pH. Sensors used in the invention contain pH sensitive indicators that give a measurable change in response to a pH change in the environment. In the embodiment in which the pH sensor is covered by a gas permeable, ion impermeable membrane, the presence of gases that effect the pH of the indicator, such as $CO_2$ or ammonia, are measured. Thus, microbial growth can be detected either by changes in pH of the liquid culture medium or by measurement of gases dissolved in a medium produced by microorganisms. Carbon dioxide is a universal metabolite produced by all organisms and, therefore, is the preferred metabolite for detection of microbial growth.

$CO_2$ and pH sensors as taught in the present invention share two common components, a molecular species useful as a pH indicator and an attachment/support medium. The pH indicator can be attached either covalently or non-covalently to the support medium. Alternatively, the indicator can be encapsulated within a polymer matrix that is gas permeable such as a pH indicator emulsified within a polymer matrix prior to curing. The $CO_2$ sensor has a third component, a semi-permeable substance that completely separates the indicator membrane from the specimen and growth medium. These sensors are fixed inside a suitable transparent vessel 1 with an appropriate adhesive.

A variety of different fluorescent and visible pH indicators can be used as the active molecular species in pH or $CO_2$ sensors. Generally, the only limitations on the selection of indicators are the requirements that they have acceptable dynamic pH ranges and exhibit wavelength changes that are readily detectable by existing front surface fluorescence or reflectance technologies.

Sensors for detecting pH changes in the culture medium according to the invention should exhibit a change in fluorescence intensity or visible color over a pH range of about 5.0 to about 8.0.

Indicators for a $CO_2$ sensor should exhibit a change in fluorescence intensity or visible color in a pH range between about 10.0 and 6.0 in order to detect changes in $CO_2$ concentrations.

Only certain pH indicator molecules can be bound covalently or non-covalently to a support medium and retain their pH indicating properties. We found indicators belonging to the xanthene, phenolphthalein and phenolsulfonphthalein groups to be useful.

The attachment/support medium can be a substance such as cellulose, to which a pH indicator can be covalently attached using organic reactions. Non-covalent attachment of pH indicators can be achieved using ionic support materials, such as nylon membranes that have a positive or negative zeta potential. Other ionic support materials that can be used are positively or negatively charged ionic resins, such as diethylamino ethyl (DEAE) resin or (DEAE) cellulose. Pretreatment of the support material with a protein may be required if the indicator membrane is to be in direct contact with the microbial growth media.

The pH indicator sensors directly detect pH changes due to the pH environment of the microbial growth medium. However, these sensors can be made to selectively react to gases (e.g., carbon dioxide or ammonia) in the liquid growth medium by covering them with a selectively semi-permeable composition or membrane such as silicon, latex, teflon or various plastics characterized by the capacity to selectively permit the diffusion of a gas while preventing the passage of ions and liquid. For sensors comprising an indicator encapsulated within a polymer matrix, the polymer forming the matrix can act as the semi-permeable barrier that permits the passage of gases, but not ions from the fluid.

In the encapsulated indicator embodiment, the $CO_2$ sensor is comprised of a visual or fluorescent pH indicator which is reactive in the pH range of 6 to 10 sodium hydroxide or an equivalent base which maintains an optimal pH environment for detection of $CO_2$, a glycerol or equivalent emulsifier which can produce micelles of indicator solution dispersed within the uncured polymer and an uncured polymer such as room temperature RTV white silicon which maintains the proper environment for the indicator. Any polymer can be used that does not affect the chemical activity of the indicator, either due to its own chemical or physical properties or its requirements for curing, as long as it is permeable to gases but not to ions from the fluid and does not have these properties altered when subjected to sterilization by autoclaving.

An emulsion is prepared from the four components above and the polymer is cured to form a semi-permeable matrix around the micelles of pH indicator, which permits selective diffusion of $CO_2$ and other gases from the liquid microbial growth medium, resulting in a measurable exposure of the indicator to provide a measurable visual change in the indicator color. The sensor 2 can be prepared separately and adhered to the interior surface of the culture bottle or, in the alternative, the sensor 2 can be formed on the bottom of the bottle and cured in situ. After curing, the bottle with the sensor is sterilized, such as by autoclaving. A number of specific examples of pH and $CO_2$ sensors are provided in co-pending U.S. patent application Ser. No. 07/168,291, filed Mar. 15th, 1988, the specification of which is incorporated herein by reference. Specific pH and $CO_2$ indicators are not herein detailed beyond the above description. The sensors must provide visually detectable indication of pH and or $CO_2$ changes in order to properly interact with the instrument and equipment described below.

Similarly, culture medium formulations are described in the co-pending application Ser. No. 07/168,291 and are therefore not detailed herein.

FIG. 1 illustrates a cross-sectional view of a culture container 1 with a sample and medium 3 therein and a sensor 2 attached to the bottom surface thereof. The container 1 is illustrated situated on a platform 7 which has an opening 8 into which is inserted photodetector 5 and an opening 9 into which is inserted emitter 4.

Figure 6:
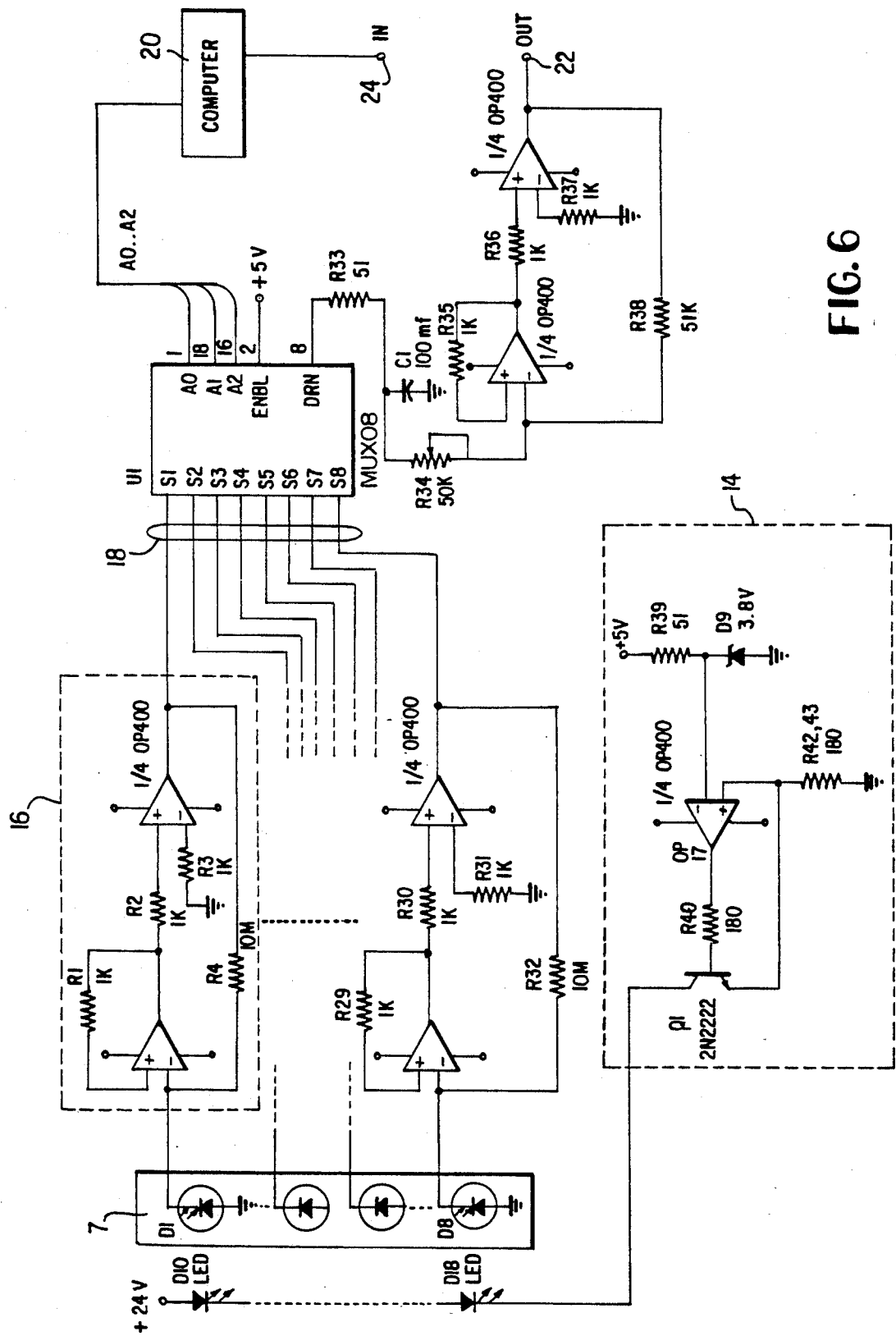
FIG. 6 is a schematic block diagram illustrating the major components of the analysis apparatus of the present invention.

Both the emitter 4 and the detector 5 are connected to the analysis apparatus 6 illustrated in greater detail in FIG. 6.

Figure 7C:
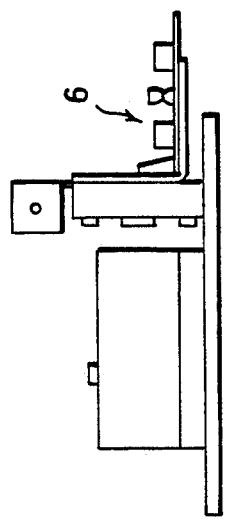
FIG. 7a-c is a perspective view of an embodiment of the present invention illustrating eight simultaneously monitored samples.
Figure 7B:
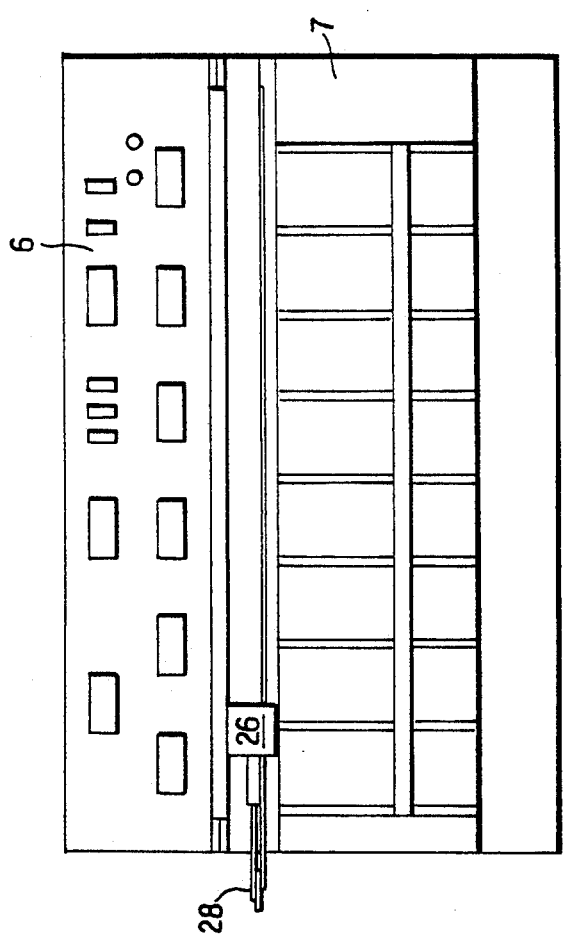
Figure 7A:
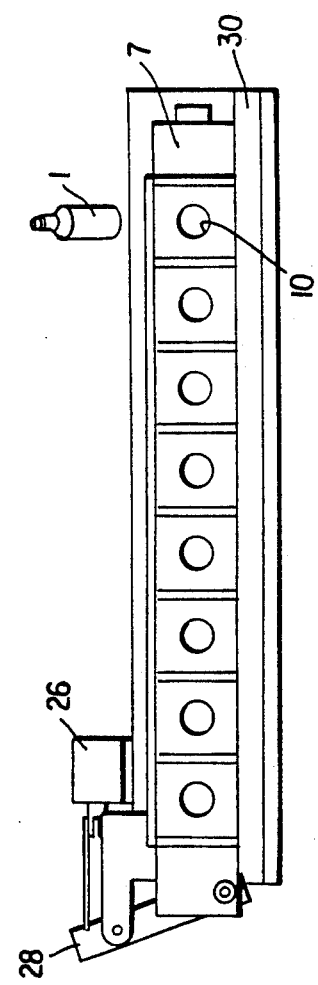

Containers 1 are generally cylindrical in form, as illustrated in FIG. 7, and fit into openings 10 in the upper surface of substrate 7. The containers 1 are maintained snugly within the openings 10 through use of resilient packing material 12. The interior of the openings 10 are lined with the packing material 12 which resiliently presses against the sidewalls of container 1, when it is fitted into the openings. This packing is provided to prevent the containers 1 from falling out of the openings 10 during motion of the substrate 7 as described below. Emitter 4 and detector 5 are mounted at a relative angle $\alpha$ to provide for optimal reception of reflected light from indicator 2. Angle $\alpha$ in the illustrated preferred embodiment is 45 degrees, however, other relative angles near 45 degrees provide acceptable results. A preferred range of 30 to 60 degree has been found optimal to give the best reflective efficiency.

The emitter 4 and detector 5 must be placed at an appropriate relative angle and at an appropriate angle relative to the indicator 2, so that the light will not reflect off the exterior of container 1 but will reach and reflect off of indicator 2. Further, the detector 5 must be shielded from direct illumination from the emitter 4 to prevent an inaccurate reading.

FIG. 7 illustrates the overall configuration of one exemplary embodiment of the present invention. As can be seen in FIG. 7, the base member 7 has a number of cylindrical slots 10 to accommodate the sample bottles 1. Any number of bottles 1 can be placed into the slots 10 in the substrate or base 7. The base 7 is mounted in a manner that it can be rocked by rocking motor 26 and rocking mechanism 28 attached thereto. The rocking is necessary to keep the mixture properly agitated and stirred within the bottles 1 to promote proper microbacterial growth. The base is also heated by means of heaters 30 which are secured to the base or by total enclosure of the base in a controlled incubation apparatus.

Each of the slots 10 includes an emitter and a detector for appropriately illuminating the sensors and detecting the reflected luminescence.

As detailed below, each of the bottles 1 can be independently monitored through selected reading of the outputs of the detectors associated with the slots into which each of the bottles have been inserted. In this manner, computer 20 can monitor a number of samples simultaneously taking a sample reading of each as desired at a pre-determined sampling rate and evaluating the microbacterial growth progress of each sample as detailed below.

FIG. 6 is a circuit diagram illustrating the signal reception and processing portion of the signal analysis device 6 illustrated in FIGS. 1 and 7. The LED's D11 through D18 are powered by a Zener-stabilized constant current source 14. The current source includes transistor Q1 operational amplifier op17 and Zener diode D9. The current source 14 provides a stable illumination for the LED's 11 through 18 illuminating diode receptors D1 through D8.

LED's D10 through D18 are representative of the light emitter 4 illustrated in FIG. 1 and photo diodes D1 through D8 are illustrative of the light detector 5 illustrated in FIG. 1.

In FIGS. 6 and 7 there are eight diodes mounted on substrate 7, four of which are illustrated. The embodiment illustrates eight light emitters, eight detectors and eight parallel circuitry paths, for exemplary purposes only. The number of emitters and detector pairs utilized depends upon the number of samples to be evaluated by a single processing apparatus 6.

The photo diodes D1 through D8 illustrated can, for example, be VTP 5051 photo diodes from EGG Vactech of St. Louis, Miss. Any comparable photo diode capable of sensitive detection in a given area of the spectrum can be utilized. Photo diodes capable of detection in other areas of the electromagnetic spectrum can be utilized if the photo emitters 4 are designed to emit in that portion of the spectrum and the sensor 2 is designed to exhibit reflective properties in that portion of the spectrum in response to changes in pH or $CO_2$ production.

The output of each diode is amplified by a pair of low offset operational amplifiers arranged in a low drive inverting configuration. This configuration is illustrated by that portion of the circuit identified as 16, in FIG. 6.

The outputs of the operational amplifiers are multiplexed into multiplexer MUX08 on individual input lines 18. In this manner the output of any one of the individual diodes D1 through D8 can be selected for monitoring and or analysis. Through provision of a three bit address provided on address lines A0 through A2, the computer 20 can select the desired diode output to be read out on DRN line 8 from multiplexer MUX08. The signal out from the multiplexer is then passively low pass filtered and amplified and provided as an analog signal output for computer 20. This analog signal at the output terminal 22 can first be converted to a digital signal and then passed to the input terminal 24 of the computer, or can be passed directly to the computer as a analog signal.

Within the computer 20, the outputs of the various detectors are compiled, and the curves characteristic of the quantity and rate of change of pH or $CO_2$ concentration of the various samples and illustrated in FIG. 5 are developed. The computer also performs the necessary analysis to evaluate the characteristics developed and to determine the presence or absence of developing microbial cultures as described below.

With reference to the graphs of FIG. 5, the advantages of the analysis technique available through the present invention over those available in the prior art or through visual inspection are described below.

Figure 5A:
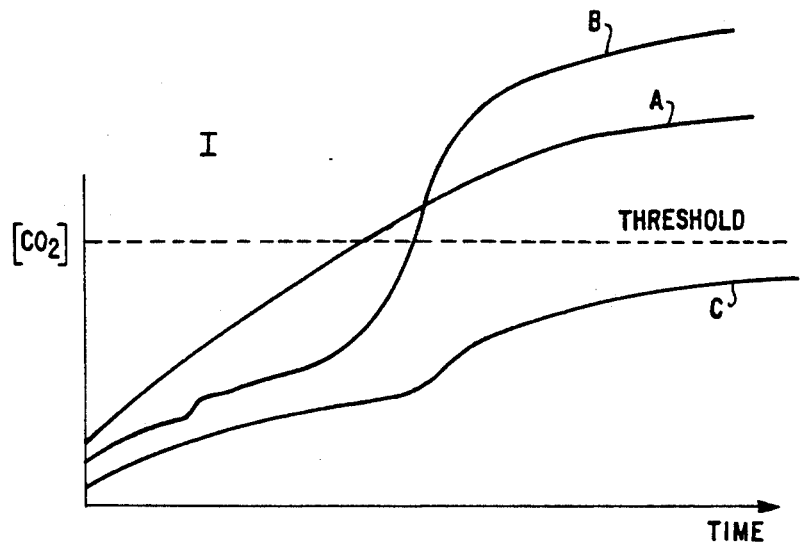
FIGS. 5a to 5c are graphs illustrating the threshold rate generation level versus constant slope monitoring detection methods.

In FIG. 5a, the absolute level of $CO_2$ has been plotted against time, along with a threshold $CO_2$ level which might be used to determine if microbial contamination was present. The absolute $CO_2$ concentration value of the solution is determined through analysis of the color change of indicator 2 within the container 1. It should be noted that bodily fluids such as blood demonstrate a production of $CO_2$ of their own, which is seen in the steadily rising levels in all three curves. The magnitude of this background production varies greatly among specimen.

Curves A, B and C represent exemplary microbial growths. Curve A illustrates a high level of background production, but no microbial growth. It crosses the threshold and would therefore be considered a positive under prior art analysis techniques, but would be a false positive. Curve B illustrates a moderate background level and strongly visible growth. Since Curve B also crosses the threshold level, it would be detected as true positive. These can be detected by periodic sampling techniques having a significant elapsed time between sampling because the $CO_2$ level remains above the threshold for a significant period of time. Curve C illustrates a combination of low background protection and poor growth, resulting in a false negative, as shown below, under prior detection analysis.

Figure 5B:
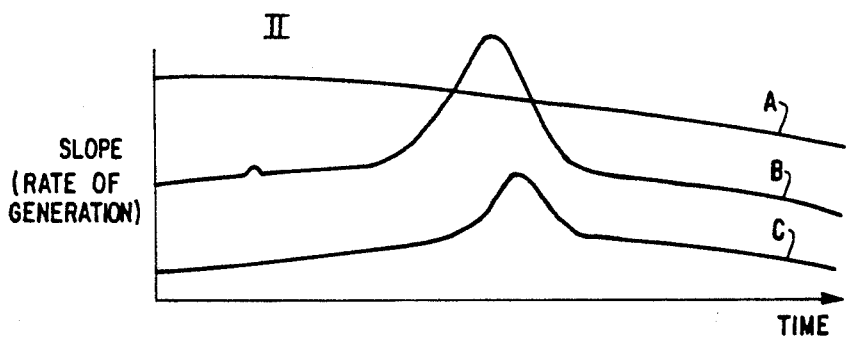

FIG. 5b illustrates the first derivative of the data in FIG. 5a, or the rate of $CO_2$ production. It can be seen that the rate of A is high but constantly decreasing; of B moderate with an increase at the time of microbial growth; and C low, but again with an increase at the time of microbial growth.

Figure 5C:
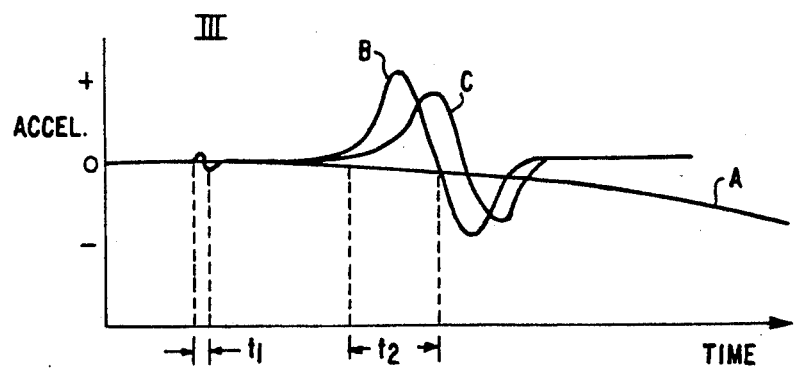

FIG. 5c illustrates the second derivative, or growth acceleration, of the data in the first graph. Here, Curve A illustrates a constantly negative acceleration, whereas B and C show periods of strongly positive acceleration. Analyzing the graphs, although the $CO_2$ value of the sample A rises above a threshold value in FIG. 5a, it does not have a rate of change in FIG. 5c and therefore signifies a lack of microbial growth. It can be seen that in FIG. 5c the two true positive samples B and C exhibit positive characteristics not present in sample A.

Curve C illustrates microbial growth exhibiting a slower $CO_2$ generation rate which can be due to a variety of factors. In this instance, through use of the sampling techniques of the prior art or through visual inspection of the indicator 2 of the present invention, this sample would be determined to be a negative which would be a false negative. This is due to the fact that the absolute $CO_2$ value of sample C never rises above a threshold value necessary to indicate a positive reading. However, if the sampling, analysis and evaluation technique of the present invention described below is utilized, this actual microbacterial growth, although not sufficient to raise the $CO_2$ of the sample above at threshold level of FIG. 5a, would be detected as a positive bacterial presence and therefore a true positive.

The computer 20 of the present invention can be set to read the indicated $CO_2$ value at any given interval. For example, when a sampling interval of ten minutes between readings is used, the computer will instruct the multiplexer MUX08 to output a reading from the appropriate sensor input at ten minute intervals. The reading will be read and recorded by the computer. The computer then takes another reading after ten minutes and records the value.

After six intervals have been stored, a seventh interval is taken and the first interval is dropped. The computer will continue to update in this manner by dropping the oldest sample and adding the most recent, so that at all times the computer has a one hour period of data at hand.

The computer 20 utilizes these samples to continuously determine the slope of the curve connecting each adjacent pair of pH readings and therefore establishes an "instantaneous" slope value between each pair of adjacent ten minute interval readings. This slope is compared to the previous interval slope and to the slopes of the intervals preceding that back to a total of six intervals or an hour. This provides the computer with the rate of generation and acceleration values represented in graphs II and III.

The slope of the present ten-minute sampling period can be compared solely against the slope of the last period or can be compared against the slope of the last five periods on a weighted basis. The computer looks for positive acceleration such as those illustrated by the curves B and C of FIG. 5c, of FIG. 5. The time duration of the positive acceleration is monitored, and the acceleration must remain positive for a period of time greater than that which could be attributed to instrument fluctuations or other background interference. For example, time period $t_1$ in FIG. 5c is insufficient whereas time period $t_2$ is sufficient.

This method of analysis is superior to the prior art because both curves B and C which have positive bacterial growth will be detected by the present invention. This analysis scheme is not dependent upon the absolute value of the $CO_2$ developed within the sample, but only depends upon a change in the rate of $CO_2$ increase which has been found to be a more reliable indicator of positive biological samples than is the crossing of a threshold by the absolute $CO_2$ value.

This method of analysis is only achievable through the apparatus and teaching of the present invention which allows for continuous monitoring and close spaced sampling and which provides an indicator 2 of sufficient sensitivity to allow for high precision $CO_2$ readings to be obtained.

The sensors monitored by this instrument contain indicators that change color when growing or metabolizing microbes are present and generate either a pH or a $CO_2$ change. Although the color changes may be apparent to the naked eye, use of the signal analysis device 6 provides the advantage of objectivity, sensitivity, and continuity of measurement. In the preferred embodiment, a light emitter and detector are provided for each sensor. However, other alternatives are available to allow continuous monitoring of all the samples. These alternatives include utilizing means to move each specimen bottle past one or more stationary detectors or to move one or more detectors past the stationary bottles.

In the preferred embodiment described above solid state illuminators and detectors are utilized; however, incandescent and arc lamp sources of illumination could also be used and mirrors, lenses, optical fibers and other means of directing the light to the indicator within the bottle for reflection to a detection means can also be utilized as would be apparent to the skilled artisan after the disclosure of the present invention. Other objects, advantages and features of the present invention will become apparent to those skilled in the art from the following discussion.

We claim:

1. An instrument for monitoring microbial growth in a specimen, comprising:
    a sealable, sterilizable container having an internal chamber in which the specimen is cultured in a sterile culture medium, the container having at least one transparent section;
    a sterilizable indicator means located in the container in the region of the transparent section, said indicator means exhibiting a change in its measurable properties detectable through said transparent section upon exposure to metabolites of microbial growth, whereby changes in the indicator means can be monitored from the exterior of the container through said transparent section, thereby monitoring microbial growth without entering the container after sealing;
    an emitter means for emitting an emitter signal that interacts with at least one measurable property of said indicator means, whereby an indicator signal is produced, positioned relative to said indicator means so that said emitter signal strikes said indicator means through the transparent section;
    a detector means positioned relative to said indicator means for receiving the indicator signal from said indicator means through the transparent section and for producing a detector signal corresponding thereto;
    processing means for receiving said detector signal and for processing said detector signal to evaluate changes in or the magnitude of the measurable property of said indicator means and thereby monitor microbial growth in said sealable container after said container has been sealed.

2. An instrument according to claim 1, wherein said processing means for receiving said detector signal is a circuit means.

3. An instrument according to claim 1, said emitter means including a light emitting diode.

4. An instrument according to claim 3, said detector means including a photodiode receptive to the indicator signal produced as a result of the emission of said light emitting diode.

5. An instrument according to claim 3, said processing means for receiving said detector signal including a stabilized current source for said light emitting diode.

6. An instrument according to claim 2, said circuit means including:
    computing means for receiving said detector signal at selected time intervals and for comparing any changes in the characteristics of said detector signal during each of said time intervals.

7. An instrument according to claim 2, said circuit means including computation means for periodic sampling of said detector signal, for comparing samples of said detector signal, and for calculating the rate of change of said samples.

8. An instrument according to claim 1 further comprising means for detecting a rate of change of a measurable property of said indicator means and for measuring the duration of said rate of change.

9. An instrument according to claim 1, wherein the indicator means comprises a membrane and an indicator medium, the indicator medium exhibiting a detectable change when exposed to microbial metabolites.

10. An instrument according to claim 9, wherein the membrane is secured to an interior wall of the container.

11. An instrument according to claim 1, wherein the indicator means is disposed against an interior wall of the container and the indicator means comprises a membrane that separates the indicator means from the culture medium.

12. An instrument set forth in claim 1, wherein the metabolite is $CO_2$.

13. An instrument according to claim 1, wherein the indicator means comprises a chemical responsive to pH.

14. The instrument set forth in claim 1, wherein said measurable property is selected from the group consisting of light absorbance, phosphorescence, light scattering, refraction, fluorescence, and light reflectance characteristics.

15. An instrument according to claim 8, further comprising means for detecting acceleration of change of a measurable property of the indicator means.

16. An instrument according to claim 15, also measuring the duration of said acceleration.

17. An instrument according to claim 1, further comprising means for measuring the magnitude of said detector signal.

18. An instrument according to claim 17, also measuring the duration of the magnitude of said detector signal.

19. A method for detecting microbial growth in a specimen, comprising the steps of:
providing a sterilizable container, the container having at least one transparent section in a wall thereof and an indicator means that changes when exposed to metabolites of microbial growth disposed in the container in the region of the transparent section;
providing an emitter means for emitting an emitter signal that interacts with at least one measurable property of said indicator means, whereby an indicator signal is produced, and positioned relative to said indicator means so that said emitter signal strikes said indicator means through the transparent section;
providing a detector means positioned relative to said indicator means for receiving the indicator signal from said indicator means and for producing a detector signal corresponding thereto;
providing a processing means for receiving said detector signal and for processing said detector signal to evaluate the change in or the magnitude of the measurable properties of said indicator means;
introducing the specimen under sterile conditions into the container;
incubating the specimen in the container; and
detecting a change in or magnitude of the detector signal, thereby detecting microbial growth in the sealable bottle after the container has been sealed.

20. A method according to claim 19, comprising the further steps of:
receiving said detector signal at selected time intervals; and
comparing any changes in the characteristics of said detector signal during said time intervals.

21. A method according to claim 19, including the further steps of:
sampling said detector signal;
comparing successive samples of said detector signal; and
calculating the rate of increase in the rate of change between successive samples.

22. A method according to claim 19, including the further steps of:
detecting a rate of change in the detector signal; and
measuring the duration of said rate.

23. The method set forth in claim 19, wherein said measurable property is selected from the group consisting of light absorbance, phosphorescence, light scattering, refraction, fluorescence, and light reflectance characteristics.

24. A method of determining the presence of microbes in a specimen, comprising the steps of:
providing the instrument of claim 1;
introducing the specimen into the sterile container;
incubating the specimen in the container;
monitoring for a change in a measurable property of the indicator means with the detector means at at least one time interval;
calculating the rate of change of the measurable property, whereby a first derivative of the property is determined; and
analyzing the magnitude of the first derivative of the measurable property to establish the presence of microbes in the specimen.

25. A method according to claim 24, including the further steps of:
calculating the second derivative of the measurable property; and
analyzing the magnitude of the second derivative of the measurable property whereby the presence of microbes in the specimen is ascertained.

26. A method according to claim 25, including the further steps of:
measuring the duration of said second derivative.

27. The method set forth in claim 24, wherein said measurable property is selected from the group consisting of light absorbance, phosphorescence, light scattering, refraction, fluorescence, and light reflectance characteristics.

28. A method of determining the presence of microbes in a specimen, comprising the steps of:
providing the instrument of claim 1;
introducing the specimen into the sterile container;
incubating the specimen in the container;
monitoring for a change in a measurable property of the indicator means with the detector means at at least one time interval; and
measuring the magnitude of the measurable property to establish the presence of microbes in the specimen.

* * * * *

UNITED STATES PATENT AND TRADEMARK OFFICE
CERTIFICATE OF CORRECTION

PATENT NO.   : 5,164,796
DATED        : November 17, 1992
INVENTOR(S)  : Di Guiseppi et al.

It is certified that error appears in the above-identified patent and that said Letters Patent is hereby corrected as shown below:

<u>Title page,</u>
Item [22], the filing date should read as follows:
-- Filed: February 1, 1991 --

Signed and Sealed this

Third Day of September, 2002

Attest:

JAMES E. ROGAN
Attesting Officer     *Director of the United States Patent and Trademark Office*